United States Patent
Warner et al.

(10) Patent No.: US 8,682,686 B2
(45) Date of Patent: Mar. 25, 2014

(54) SYSTEM AND METHOD TO MANAGE A WORKFLOW IN DELIVERING HEALTHCARE

(75) Inventors: Adrian Warner, Delafield, WI (US); Crispian Sievenpiper, Waukesha, WI (US); Jeffery Solliday-McRoy, Menominee Falls, WI (US)

(73) Assignee: General Electric Company, Schenectedy, NY (US)

( * ) Notice: Subject to any disclaimer, the term of this patent is extended or adjusted under 35 U.S.C. 154(b) by 1100 days.

(21) Appl. No.: 11/972,878

(22) Filed: Jan. 11, 2008

(65) Prior Publication Data

US 2009/0182575 A1 Jul. 16, 2009

(51) Int. Cl.
*G06Q 50/00* (2012.01)

(52) U.S. Cl.
USPC ............. 705/2; 705/7.22; 705/7.25; 705/7.27

(58) Field of Classification Search
CPC ....... G06Q 10/06; G06Q 50/22; G06F 19/327
USPC ................................. 705/2/3, 2–4, 7.25, 7.27
See application file for complete search history.

(56) References Cited

U.S. PATENT DOCUMENTS

| | | | | |
|---|---|---|---|---|
| 6,006,191 | A * | 12/1999 | DiRienzo | 705/2 |
| 6,091,998 | A | 7/2000 | Vasko et al. | |
| 6,801,819 | B1 | 10/2004 | Barto et al. | |
| 6,954,148 | B2 | 10/2005 | Pulkkinen et al. | |
| 2004/0019501 | A1 | 1/2004 | White et al. | |
| 2004/0138925 | A1 * | 7/2004 | Zheng | 705/2 |
| 2004/0249676 | A1 | 12/2004 | Marshall et al. | |
| 2005/0018928 | A1 | 1/2005 | Paul et al. | |
| 2005/0055256 | A1 * | 3/2005 | Scott | 705/8 |
| 2005/0075906 | A1 * | 4/2005 | Kaindl et al. | 705/2 |
| 2005/0080658 | A1 * | 4/2005 | Kohn et al. | 705/8 |
| 2005/0267367 | A1 | 12/2005 | Kerby et al. | |

(Continued)

FOREIGN PATENT DOCUMENTS

| | | |
|---|---|---|
| WO | 2006093544 | 9/2006 |
| WO | 20060116529 | 11/2006 |

OTHER PUBLICATIONS

Biswas and Merchawi, "Use of Discrete Event Simulation to Validate an Agent Based Scheduling Engine," Delimis Corporation, Proceedings of the 2000 Winter Simulation Conference, pp. 1778-1782.

(Continued)

*Primary Examiner* — Mark Holcomb
(74) *Attorney, Agent, or Firm* — Hanley, Flight and Zimmerman, LLC

(57) ABSTRACT

A system and method to manage progression of patients through a workflow of events that employs at least one resource in delivering healthcare is provided. The system comprises a sensor operable to track at least one property of the plurality of patients, and at least one processor in communication with the sensor. The processor is operable to execute computer readable program instructions generally representative of the steps of calculating a bid of the more than one of series of resources relative to one another directed to a slot in the schedule of workflow of the patient dependent on tracked properties of the resources, and assigning one the resources to the slot in the schedule of workflow of the least one patient dependent on a comparison of the bid of the resources relative to one another.

19 Claims, 7 Drawing Sheets

(56) References Cited

U.S. PATENT DOCUMENTS

| | | | |
|---|---|---|---|
| 2006/0109961 | A1 | 5/2006 | Mahesh et al. |
| 2006/0143044 | A1* | 6/2006 | Conry et al. ............ 705/2 |
| 2007/0055557 | A1 | 3/2007 | Kloppmann et al. |
| 2007/0087756 | A1 | 4/2007 | Hoffberg |
| 2007/0129983 | A1 | 6/2007 | Scherpbier et al. |
| 2007/0136089 | A1 | 6/2007 | Schneider et al. |
| 2007/0185730 | A1 | 8/2007 | Mahesh et al. |
| 2007/0208604 | A1* | 9/2007 | Purohit et al. ............ 705/9 |
| 2007/0226008 | A1* | 9/2007 | Halsted et al. ............ 705/2 |
| 2007/0282476 | A1 | 12/2007 | Song et al. |
| 2009/0182576 | A1 | 7/2009 | Warner et al. |

OTHER PUBLICATIONS

"Game Theory," <http://pespmc1.vub.ac.be/Asc/GAME_THEOR.html> (Jan. 2, 2008).

"Game Theory," <http://en.wikipedia.org/wiki/Game_theory> (Jan. 2, 2008).

Erik W. Weissteng "Game Theory," Mathworld-A Wolfram Web Resource, <http://mathworld.wolfram.com/GameTheory.html> (Jan. 2, 2008).

Siemans, "Soarian Scheduling," <http://www.medical.siemens.com/webapp/wcs/stores/servlet/ProductDisplay~q_catalogId~e_-1~a_catTree~e_100010,1008631,1007111,1007092,1007099,1007204~a_langId~e_-1~a_productId~e_173523~a_storeId~e_10001.htm> (Jan. 2, 2008).

Philips, Press Release; "New Philips IT solutions for hospital and cardiac care suites designed to enhance clinicians' ability to diagnose and treat patients," <www.medical.philips.com/us/news/content/file_1455.html> (Feb. 26, 2007).

"BPM Research History—From Office Automation to Workflow Management," <www.bpm-research.com/research/history-of-bpm-and-workflow/research/> (Jan. 3, 2008).

Michael Zur Muehlen, "Workflow-Based Process Controlling—Foundation, Design, and Application of Workflow-driven Process Information Systems," Workflow-based Process Controlling, Logos Verlag—Berlin (2004) pp. 1-12.

Zenios, Chertow and Wein, "Dynamic Allocations of Kidneys to Candidates on the Transplant Waiting List," Operations Research, vol. 48, No. 4 (Jul.-Aug. 2000) pp. 549-569.

PCT International Search Report and Written Opinion mailed Oct. 29, 2010 for PCT International Application No. PCT/US2008/086010.

* cited by examiner

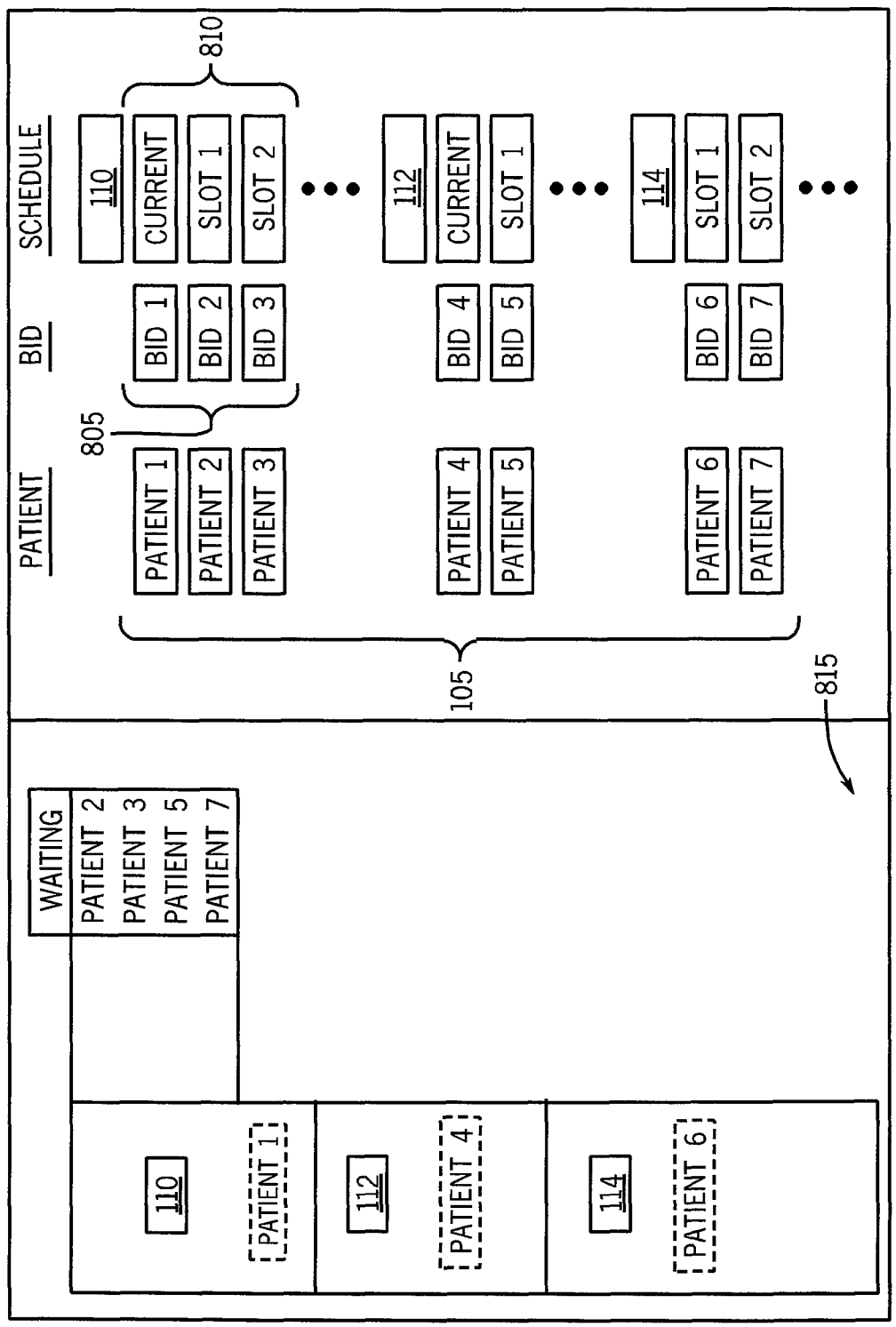

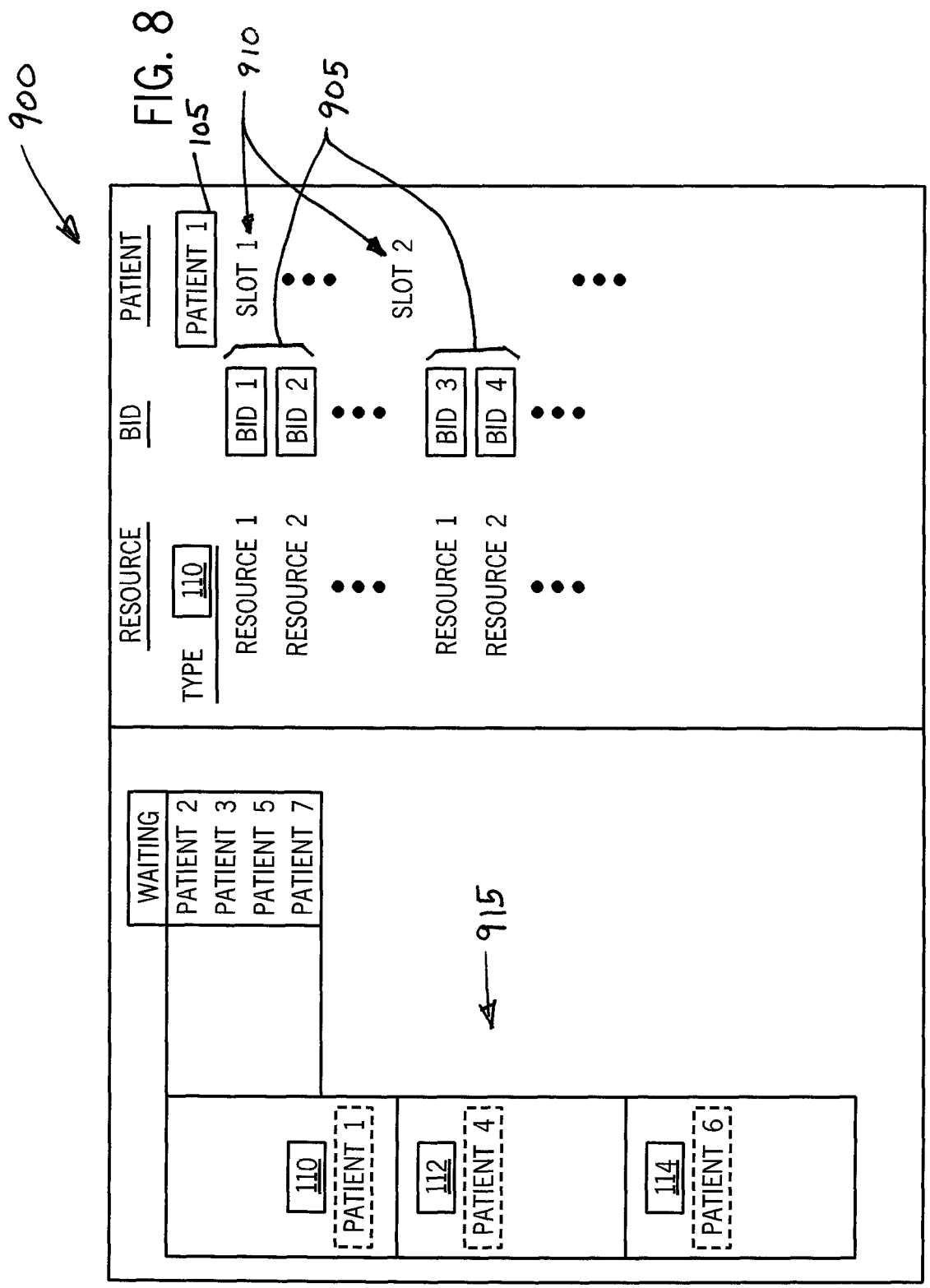

SYSTEM AND METHOD TO MANAGE A WORKFLOW IN DELIVERING HEALTHCARE

RELATED APPLICATIONS

This application is related to U.S. application Ser. No. 11/972,888 entitled "A SYSTEM AND METHOD TO MANAGE A WORKFLOW IN DELIVERING HEALTHCARE", filed simultaneously with this application and hereby incorporated herein by reference in its entirety.

BACKGROUND

The subject herein generally relates to a system and method to manage progression of a patient through a workflow, and in particular, the workflow is a healthcare procedure.

Hospitals and other medical facilities (e.g., imaging centers, cardiology treatment centers, emergency rooms, surgical suites, etc.) include various workflows to deliver diagnosis or treatment to admitted patients. These workflows are comprised of events that employ various resources, such as imaging rooms, physicians, nurses, radiologists, cardiologists, clinicians, technicians, or transcriptionists. These workflows are often unstructured and non-linear in nature due to complex conditions that dynamically evolve at any point in time of the workflow.

Known systems and methods to manage patients through these workflows delivered at healthcare facilities are generally static and non-adaptive. These known systems generally rely on past data and linear design assumptions to manage workflows (e.g., diagnostic imaging, cardiac treatment, etc.). As a result, these known systems and methods are generally inflexible or unresponsive to non-linear changes or events that increase the likelihood of chaos due to complex conditions that evolve in real time beyond the original linear design. Examples of parameters to measure a quality of service or efficiency of workflows include, but are not limited to, patient wait times, procedure turn-around times, resource utilization, etc. For example, increasing procedure turn-around times can increase underutilization of resources (e.g., an imaging room sitting idle).

BRIEF SUMMARY

Thus, there exist a need for a system and method for real-time medical/clinical workflow management and optimization. The system needs to be multi-variant to address variation demand and urgency, diverse procedure goals, custom workflows without standard work times, unused capacity, excess waiting by patients, and delay of critical decision making due to lack of critical information. The above-mentioned problems and needs are addressed by the subject matter described herein in the following description.

According to one embodiment, a system to manage progression of a plurality of patients through a workflow of events that employs a plurality of resources is provided. The system comprises at least one sensor operable to track at least one property of more than one of the plurality of resources; and at least one processor in communication with the at least one sensor. The at least one processor is operable to execute a plurality computer readable program instructions generally representative of the steps of calculating a bid of the more than one of the plurality of resources relative to one another directed to a slot in the schedule of workflow of the at least one patient, the bid dependent on the at least one tracked property of the more than one of the plurality of resources, and assigning one of the more than one resource to the slot in the schedule of workflow of the least one patient dependent on a comparison of the bid of the more than one resource relative to one another.

According to another embodiment, a method to manage progression of at least one patient through a workflow of events that employs a plurality of resources, comprising tracking at least one property of more than one of the plurality of resources; calculating a bid of the more than one of the plurality of resources relative to one another directed to a slot in a schedule of the workflow of the least one patient, the bid dependent on the at least one tracked property of the more than one resources; and assigning one of the more than one resource to the slot in the schedule of workflow of the least one patient dependent on a comparison of the bid of the more than one resource relative to one another.

According to yet another embodiment, a dashboard to manage progress at least one patient through a workflow of events in delivering healthcare is provided. The dashboard comprises an illustration of an identifier of at least patient; and an illustration of an identifier of each of the more than one resources designated to be utilized on the patient progressing through the events of the workflow, the illustrations of identifiers of the more than one resources arranged according to an order of value of a bid of each of the more than one resources directed to utilization on the at least one patient in the workflow.

Various other features, objects, and advantages of the invention will be made apparent to those skilled in the art from the accompanying drawings and detailed description thereof.

BRIEF DESCRIPTION OF THE DRAWINGS

FIG. 7 is illustrative of an embodiment of a dashboard operable to report an output of the system at any point in time of a patient progressing through the workflow.

FIG. 8 is illustrative of another embodiment of a dashboard operable to report an output of the system at any point in time of a patient progressing through the workflow.

DETAILED DESCRIPTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

Figure 1:
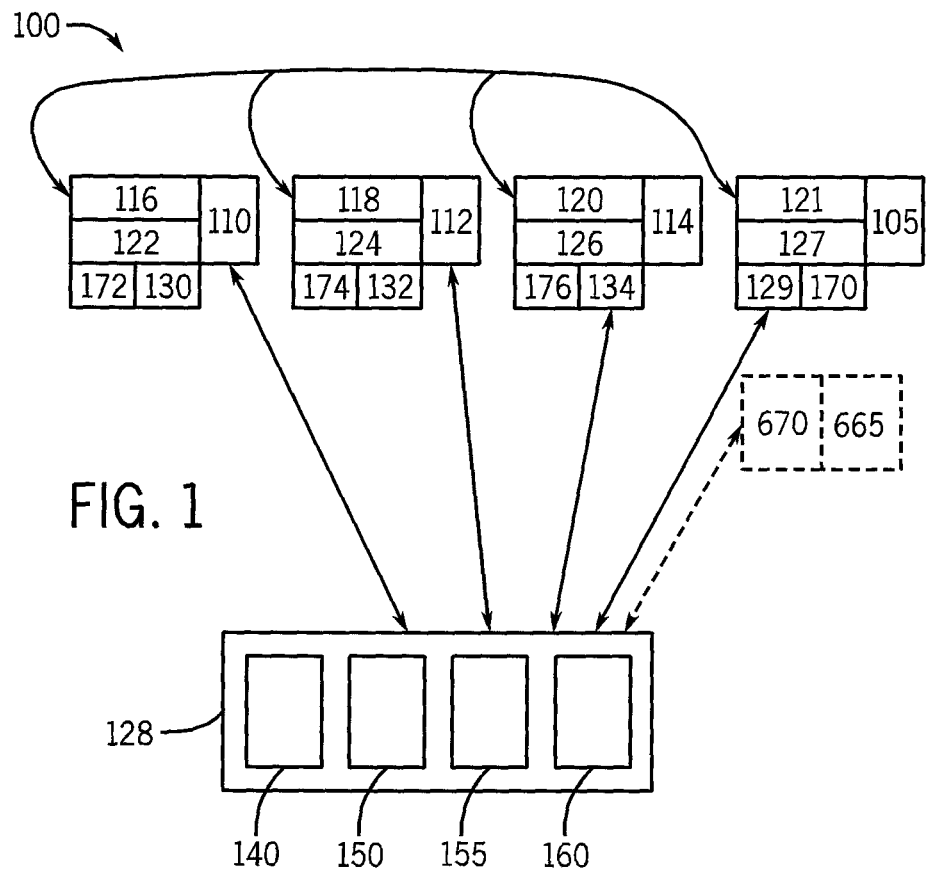
FIG. 1 is a diagrammatic overview of an embodiment of system to manage a workflow.

FIG. 1 illustrates a schematic diagram of an embodiment of a system 100 to manage a patient 105 through a workflow having an increased probability or likelihood toward chaos due to complex, non-linear conditions. The complex conditions can evolve in general real time beyond an original or predetermined design before the start of the workflow.

An embodiment of workflow as herein used can generally be defined as an embodiment of a sequence of tasks or states or steps or events (e.g., physician examination, laboratory tests, acquire electrocardiogram (ECG) data, etc.) that may or may not employ use or operation or involvement of a series of resources 110, 112, 114 to deliver a defined outcome (e.g., treatment of the patient 105 for chest pain, broken arm, trauma, illness, etc.). The number of resources 110, 112, 114 can vary. An embodiment of the resources 110, 112, 114 can be operable to interact with each other in general real-time, as well as be operable to establish a logical relationship among one another. The resources 110, 112, 114 may be included at the beginning of the workflow or in general real time during or between the events or steps of the workflow. One embodiment of the resources 110, 112, 114 include a physician 110, an imaging or scanning system 112, and a laboratory device 114. Yet, the resources 110, 112, and 114 can include test laboratories, etc. or any imaginable element involved in treatment or study of the patient 105.

An embodiment of each of the series of resources 110, 112, 114 and the patient 105 can be assigned with at least one property 116, 118, 120, 121, respectively. The type and number of properties 116, 118, 120, 121 can vary. The properties 116, 118, 120, 121 may be static so as to remain the same throughout the workflow. The properties 116, 118, 120, 121 can also be dynamic with an ability to change with time. For example, an "elapsed time" can be one of the properties 116, 118, 120, 121. Generally, the properties 116, 118, 120, 121 are predetermined prior to or at the beginning of the workflow. However, the properties 116, 118, 120, 121 can be identified or added while executing the workflow in general real-time. For example, one or more properties 116, 118, 120, 121 can be added to track a chaos or unpredictability of the availability of the resources 110, 112, 114 or events in the workflow. Another example of tracked properties 116, 118, 120, 121 include the capacity of technicians, capacity of physicians, capacity of facility, or any element involved in the workflow. Another example of the workflow in the clinical environment includes an investigational study where resources 110, 112, 114 include an ultrasound system 110 and an ultrasound operator 112 to perform a cardiac exam, where the ultrasound operator's skill and knowledge of anatomy is employed to gather the medical information from or for the study. In each case, wait times and lists of the series of patients 105 can vary in a non-linear manner.

An agent 122, 124, 126, 127 generally includes computer-readable program instructions in or not in combination with one or sensor devices (e.g., clocks, timers, blood pressure monitors, electrocardiogram (ECG) monitors, temperature monitors, etc.) created to correlate with each resource 110, 112, 114 or the patient 105, respectively. Each agent 122, 124, 126, 127 is generally operable to track or identify changes in the properties 116, 118, 120, 121 associated with each of the resources 110, 112, 114 and the patient 105, respectively. The agents 122, 124, 126, 127 can be created upon introduction or creation of the respective resource 110, 112, 114 or patient 105 into the workflow. The agents 122, 124, 126, 127 are generally operable to communicate or collaborate in general real-time with one another, as well as with the respective resources 110, 112, 114 or patient 105. FIG. 1 shows the agents 122, 124, 126, 127 located at the respective resource 110, 112, 114 or the patient 105, respectively. Yet, it should be understood that one or more of the agents 122, 124, 126, 127 can otherwise be located at a central controller or server 128.

One embodiment of the agents 122, 124, 126, 127 are configured to sense, detect, or track a presence and an awareness. Presence generally refers to an ability of the agent 122, 124, 126, 127 to express or communicate a current state of activity (e.g., available, partially in-use, fully in use, etc.) of itself to other agents 122, 124, 126, 127 in the system 100. For example, presence can include identifying or detecting whether another particular agent(s) 122, 124, 126, 127 is available, and if available, to communicate or collaborate its availability to the particular agent(s) 122, 124, 126, 127. Awareness generally refers to an ability of the agent 122, 124, 126, 127 to sense a presence of other agents 122, 124, 126, 127 or resources 110, 112, 114 or patients 105 in the system 100. For example, awareness can include an ability to track the activities of other resources 110, 112, 114 or patients 105 in the workflow. The combination of presence and awareness enables each agent 122, 124, 126, 127 to initiate a communication with one another to identify or calculate a length of time to get a response from one another. Awareness also allows the agent 122, 124, 126, 127 initiating a communication to make decisions about mode of communication (e.g., route, wireless versus wired connection, etc.) to establish contact. An ability to express or communicate the presence and leverage the awareness allows the agents 122, 124, 126, 127 to initiate communications with one another and to respond to communications from other agents 122, 124, 126, 127.

Examples of agents 122, 124, 126, 127 can receive/communicate patient data, receive/communicate requests for a work order and a report status, receive/communicate patient notifications to report for an event or step in the workflow (e.g., testing, imaging), and receive/communicate problems. Examples of agents 122, 124, 126, 127 are also operable to contact respective physicians waiting for critical patient information using an identified best mode of communication (e.g., beeper, home telephone, email, cellular phone, text message, etc.). Additionally, physicians 110 or patients 105 can communicate via computer messaging systems or other known type of input (e.g., keyboard, touch-screen, voice recognition, etc.) with the agents 122, 124, 126, 127 in the workflow community to gain access to information and collaborate with agents 122, 124, 126, 127 at any given point in time of the workflow.

An embodiment of the agents 122, 124, 126, 127 can be configured to collaborate in calculating or assigning a priority status 129 of each patient 105 to one or more available the resource 110, 112, 114 employed in the workflow relative to other patients 105. Vice versa or in addition, the agents 122, 124, 126, 127 can be configured to collaborate in calculating priority statuses 130, 132, 134 of each resource 110, 112, 114 to each patient 105. Of course, the number of priority statuses 129, 130, 132, 134 can vary with the number of resources 110, 112, 114 and patients 105. The priority statuses 129, 130, 132, 134 are created or assigned via the collaboration or communication of the agent 122, 124, 126, 127. The agents 122, 124, 126, 127 collaborate with one another to calculate or create the priority status the patient 105 for each resource 110, 112, 114 dependent on miscellaneous factors, including but not limited to, the tracked properties 116, 118, 120, 121 of all the resources 110, 112, 114 and the patients 105 in the system 100 tracked in general real-time or any given point in time of the workflow. A technical effect of the priority status 129, 130, 132, 134 is to generally define the criticality of each patient 105 relative to one another with respect to each of the resources 110, 112, 114 at any given point of time, or vice versa, the priority of each resource 110, 112, 114 to each patient 105 at any point in time. The agents 122, 124, 126, 127 can dynamically re-assign or re-set the priority statuses 129, 130, 132, 134 at generally any point in time of the workflow. If a new resource is added in the workflow, a new agent is assigned or created for that new resource, where the new agent tracks the one or more properties of the new resource with time and interacts or collaborates with other agents 122, 124, 126, 127 to calculate the priority status of each relative to one another.

For example, the agents 122, 124, 126 can track the number of uses or operations of the resources 110, 112, 114 of the system 100. After detecting a predetermined number of uses, the agents 122, 124, 126 can automatically communicate a signal to other agents 122, 124, 126, 127 that one or more of the resources 110, 112, 114 is not available (e.g., maintenance, end of life, etc.), or create a purchase order or lease request for its replacement resource 122, 124, 126. The series of agents 122, 124, 126, 127 can include, or the system 100 can further include, an additional agent having a general ability to supervise or track all of the resources 110, 112, 114 and patients 105 in the workflow, and identify or detect for errors (e.g., critical patient needs or wait time not being met in a timely manner).

The embodiment of the workflow management system 100 further includes an assessment or bidding engine 140. Although the bidding engine 140 is illustrated at the central server or computer 128, it should be understood that the bidding engine 140 can be located at any of the resources 110, 112, 114 of the system 100. An embodiment of the bidding engine 140 is generally operable to create or calculate or generate an assessment index or bid. One embodiment of the bid is a value indicative of a priority status of each patient 105 relative to one another directed to a slot in the schedule of operation or utilization of one or more of the resources 110, 112, 114. Vice versa, the assessment index or bid can include a value representative of a value of priority status of allocation of each resource 110, 112, 114 to each patient 105 relative to the other resources 110, 112, 114. Another embodiment of the assessment index or bid is generally representative of a value of patient risk or criticality of if not to receive treatment by or have access to (e.g., a slot in the schedule) one or more of the resources 110, 112, 114 relative to other patients 105. The more critical a health condition of the patient 105 or the greater a wait time of the patient 105 generally results in a greater value of patient risk or criticality relative to others. Yet another embodiment of the assessment index or bid generally represents a value or amount indicative of an availability each resources 110, 112, 114 (e.g., readiness to utilize (clean, not due for maintenance, not failed), location relative to patient, etc.) relative to the others as to be employed on each patient 105 in one or more steps in the workflow.

The bidding engine 140 generally calculates or creates each bid dependent on a series of factors, including the current priority status 129, 130, 132, 134 assigned or created for each patient 105 or each resource 110, 112, 114, and a wait time of each patient 105 for each resource 110, 112, 114. In an example, the bidding engine 140 calculates the bids in general real-time (e.g., at any point in time) dependent on the priority status of each patient 105, which is calculated at registration and updated or created with detected changes in the properties 116, 118, 120 of each of the resources 110, 112, 114 as tracked and communicated by the agents 122, 124, 126, respectively.

The bidding engine 140 can communicate with the agents 122, 124, 126 to receive the priority statuses 130, 132, 134 to each resource 110, 112, 114. Alternatively, the bidding engine 140 can collaborate in combination with the agents 122, 124, 126 to create or calculate the priority status of each resource 110, 112, 114 to each patient 105. Once the bidding engine 140 receives or creates the priority statuses 130, 132, 134, the bidding engine 140 calculates a bid dependent on a set of bidding policies for each available resource 110, 112, 114 employed in the workflow. Dependent on the value of each of the bids and the number of patients 105, the bidding engine 140 also calculates or adjusts the slots in the schedule to use or access each resource 110, 112, 114. The bidding engine 140 can dynamically update or change or recalculate (e.g., continuously or periodically) the schedule of the resources 110, 112, 114 with changes in their priority statuses, which can be correlated to or dependent on changes in the properties 116, 118, 120 (e.g., downtime for failure or routine maintenance, utilization, etc.) of each of the resource 110, 112, 114, respectively, at any point in time in the workflow.

The system 100 can also include a broker 150 in communication or combination with the bidding engine 140. An embodiment of the broker 150 generally evaluates which of the series of patients 105 holds the highest bid to each of the resources 110, 112, 114. A technical effect of the broker 150 is generally operable to optimize (e.g., reduce overall wait time of patients, allocate resources for greatest utilization, etc.) the workflow dependent on a series of factors, including the bids calculated or created for each resource 110, 112, 114, the availability of resources 110, 112, 114, and the available viable options. The broker 150 can be located with any of the resources 110, 112, 114 or at the central server 128. One embodiment of the broker 150 is operable or configured to change one or more properties 116, 118, 120, 121 of the resources 110, 112, 114 or patient 105, respectively, or change one or more of the bids generated by the bidding engine 140, dependent on tracked changes to the properties 116, 118, 120, 121 of the patient 105 or to one or more of the resources 110, 112, 114. For example, some of the properties 116, 118, 120, 121 may become insignificant with time. The broker 150 can configure or communicate with the agents 122, 124, 126, 127 to end or discard tracking of insignificant properties at any point in time.

Another embodiment of the broker 150 is generally operable or configured to alter, modify, suggest, or cancel steps or events in the workflow dependent on the priority status 130, 132, 134 of each patient 105 to the one or more resources 110, 112, 114. Assume, for sake of example, that the agent 127 of the patient 105 in a clinical workflow tracks the property 121 generally representative or indicative of a senior citizen of physical condition such that undergoing a treadmill test is undesired. In response to identifying or detecting this property 121, the broker 150 can modify the workflow to skip the step of the treadmill test in the workflow. The broker 150 can be further configured to change the schedule or priority status 130, 132, 134 to the otherwise scheduled resources 110, 112, 114 according to the detected change in the properties 116, 118, 120, 121.

Assume, for another sake of another example, that resource 114 employed in the workflow (e.g., clinical procedure) is a scanner, and that the scanner agent 124 has detected or identified that the tracked scanner property 118 is indicative that the scanner 112 has failed or is overloaded or otherwise generally unavailable. The broker 150 is generally operable to re-calculate bids of each patient 105 in view of alternative options to provide treatment to the patient 105 at a minimal cost. For example, the broker 150 can locate another resource (e.g., search inventory) having the same or similar function as the scanner 114 that is available for use (e.g., identify another imaging room with another available scanner). The property 118 being tracked by the scanner agent 124 can include a capacity of the scanner 112, and another property 121 tracked by the agent 127 can include a tracked wait time to use the scanner 112. The updates or changes to the tracked values or statuses of these properties 116, 118, 120, 121 directed to capacity or waiting time can be communicated to the bidding engine 140 or broker 150. In response, the broker 150 can re-create or adjust the schedule of each respective patient 105 or resource 110, 112, 114, the broker 150 can change one or more bidding policies that constrain or define boundary conditions of the bidding engine 140, or the broker 150 can change the workflow to skip the event or step involving the scanner 112, or the broker 150 can create a purchase order or lease request for an additional resource similar in function to the scanner 112.

An embodiment of the broker 150 can be further configured to modify an operational profile of one or more of the resources 110, 112, 114 or the patient 105. An embodiment the broker 150 can also be configured to change the measured values or the tracking of the properties 116, 118, 120, 121 in relation to time or the workflow. For example, if the wait time of any one patient 105 exceeds more than the maximum set time, the broker 150 can change the one or more properties 116, 118, 120, 121 of, or the bid calculated for, each of the patients 105 so as to selectively cause an increase or decrease in the priority status of any one patient 105 exceeding in wait time relative to other patients 105. To accomplish this, upon detecting the wait time of one patient 105 to exceed the threshold of wait time, the broker 150 calculates the bid of the one patient 105 tracked that exceeds in wait time with a bid of value greater than, or calculate the bid value to be an order or more of magnitude greater than, the bid value of any other patient 105.

For example, assume the resource 112 is generally representative of a buyer, and resource 114 is generally representative of a supplier. The suppliers 114 provide various services, and the buyers 112 avail to the service of the suppliers 114. The suppliers 114 and the buyers 112 have respective properties 118, 120 and the agents 124, 126 track or measure the properties 118, 120 or changes thereto at any instant of time. The agents 124, 126 collaborate or communicate with one another to calculate or create a priority status of each buyer 112 and supplier 114 relative to one another. The bidding engine 140 receives the priority statuses for the buyers and suppliers 112 and 114, and dependent thereon creates a schedule for the services provided by the suppliers 114 to avail to the buyers 112. Accordingly, rather than being driven solely by the next sequential task, the system 100 is also operable to schedule and manage the workflow according to other factors, including a capacity of the resources 112, 114 employed in the workflow relative to one another.

The system 100 is generally operable via the agents 122, 124, 126, 127 to track the dynamics of individual or population of patients 105 over time and their respective needs and demands on other resources 112, 114. Objective functions of the system 100 include increasing an "efficiency" from a standpoint of the healthcare or service provider, and increase an "equity" (e.g., wait time) from a standpoint of the patient 110 in the workflow managed by the system 100. The bidding engine 140 and broker 150 are operable to communicate or collaborate with one another and the agents 122, 124, 126, 127 to create or adjust the bidding policies or the workflow so as to select the optimal bidding policy for the workflow. The system 100 is generally operable in continuous time and continuous space.

An embodiment of the controller 128 is connected in communication with each of the agents 122, 124, 126, 127, bidding engine 140 and broker 150. An embodiment of the controller 128 includes a memory or database 155 generally operable to receive updated values or measurements of tracked properties 116, 118, 120, 121 on a continuous or periodic basis of the resources 110, 112, 114 or patient 105, respectively, receive new proprieties with respect to new resources or additional patients 105, bids of each patient 105 for each of the resources 110, 112, 114 at a point or instant of time of the workflow, a calculated schedule, etc.

The controller 128 can also include a processor 160 generally configured to execute program instructions store in the memory 155. Although the memory 155 and processor 160 are shown at the computer 128, it should be understood that an embodiment of the agents 116, 118, 120, 121, the bidding engine 140, or the broker 150 described above can each include processors in communication with memory or storage medium of computer-readable program instructions located at one of the resources 110, 112, 114.

An embodiment of the system 100 may further include a series of a means of sensing or sensors 170, 172, 174, 176 operable to track a location of each patient 105 or resource 110, 112, 114, respectively, with respect to a reference or to one another. An embodiment of each sensor 170, 172, 174, 176 is operable to communicate a location of each patient 105 relative to a predetermined reference. The sensors 170, 172, 174, 176 can be operable to track in coordinates, or by room or floor number, etc. The sensors 170, 172, 174, 176 can be in wireless communication with a receiver 180 connected in communication with the controller 128. An embodiment of the sensors 170, 172, 174, 176 can include a combination of transmitters in electromagnetic communication with receivers, transmitters in communication with receivers directed to radio frequency identification (RFID), optical sensors, global positioning system (GPS) in communication with satellite(s), etc. or other position measuring or locating technology known in the art or combination thereof.

Figure 2:
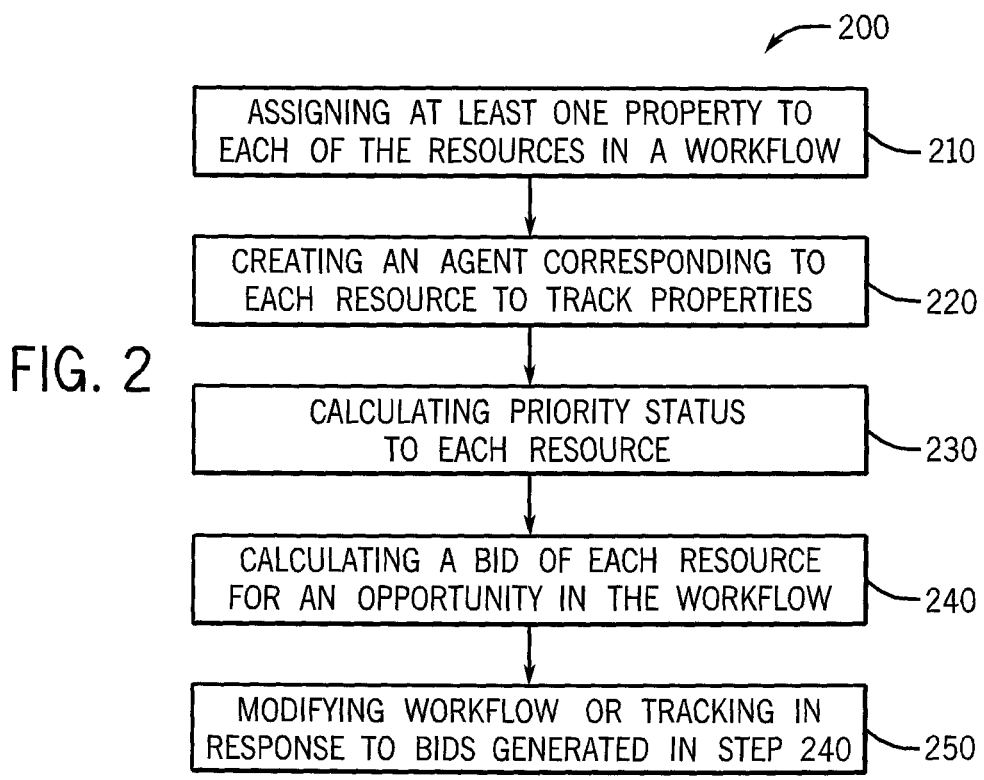
FIG. 2 is a flowchart illustrating an embodiment of a method to manage the workflow with the system of FIG. 1.

FIG. 2 includes a schematic flow diagram illustrating an embodiment of a method 200 of operation of the system 100 to dynamically manage (e.g., scheduling) the patient(s) 105 through events of the workflow that employs the series of resources 110, 112, 114. It should also be understood that the sequence of the acts or steps of the method 200 as discussed in the foregoing description can vary. Also, it should be understood that the method 200 may not require each act or step in the foregoing description, or may include additional acts or steps not disclosed herein. It should also be understood that one or more of the steps of the method 200 can be represented as computer-readable program instructions for execution by one or more processors of the agents 122, 124, 126, 127, the bidding engine 140, the broker 150, or the central server 128.

Step 210 includes assigning or identifying the properties 116, 118, 120, 121 to each of the patients 105 or resources 110, 112, 114 identified as employed in the workflow. An embodiment of step 210 includes identifying various steps or events involved in the workflow, and identifying the resources 110, 112, 114 and patients 105 involved in the steps or events of the workflow. The patients 105 or resources 110, 112, 114 and respective properties 116, 118, 120, 121 can also be identified or added at any point or instant in time of the workflow.

Step 220 includes identifying or creating the agent 122, 124, 126, 127 corresponding to each resource 110, 112, 114 and the patient 105. An embodiment of the agents 122, 124, 126, 127 are configured to track at least one property 116, 118, 120, 121 (e.g., dynamic property) of the patients 105 or resources 110, 112, 114 at any point in time of the workflow. The agents 122, 124, 126, 127 are further configured to track and communicate measurements of the tracked properties 116, 118, 120, 121 relative to one another and any changes thereto in generally real-time (e.g., continuously or periodically updated through workflow). The agents 122, 124, 126, 127 are further configured to collaborate or communicate the tracked status or values of the properties 116, 118, 120, 121 with one another via general direct or indirect interaction or communication among the agents 122, 124, 126, 127 or the resources 110, 112, 114 involved in the workflow.

Step 230 includes calculating or creating the priority status of each patient 105 to each resource 110, 112, 114. Vice versa, step 230 can include calculating or creating the priority status of each resource 110, 112, 114 to each patient 105. One embodiment of step 230 includes each agent 122, 124, 126, 127 tracking different properties 116, 118, 120, 121 of the resources 110, 112, 114 or patient 105 to which it is associated. The agents 122, 124, 126, 127 can also be operable to communicate the tracked values or states of the properties 116, 118, 120, 121 of the respective resources 110, 112, 114 or patient 105 relative to one another. By collaborating or communicating with one another or the resources 110, 112, 114 or patient 105, the agents 122, 124, 126, 127 calculate or assign or identify a priority status of the patient 105 to each resource 110, 112, 114 relative to other patients 105.

Step 240 includes the bidding engine 140 calculating the bid of each patient 105 to each of the resources 110, 112, 114, or vice versa, calculating a bid of each resource 110, 112, 114 to each patient 105, in a general bidding process, dependent on the priority statuses calculated in step 230. The bidding engine 140 generally co-ordinates this bidding process for each of the one or more events of the workflow. One embodiment of the bidding engine 140 calculates the bid of each patient 105 to each resource 110, 112, 114 depending on a series of factors or bidding policies, including but not limited to, the received priority status of the patient 105 as calculated by each agent 127, capacity of the resources 110, 112, 114 or workflow, a wait time of any individual patient 105, and an availability or status of utilization (e.g., clean, due for maintenance, failed condition, inventory, in use, etc.) of the resources 110, 112, 114 that can limit or place a boundary condition on the bidding process, and a sequence of the workflow. For example, the bidding engine 140 can calculate or simulate a plurality of the possible combinations of allocations of resources 110, 112, 114 to be employed in the workflow per the patients 105 in the workflow, and calculate one of the plurality of possible or candidate combinations that best optimizes (e.g., minimum patient wait time, maximum throughput capacity, lowest cost, etc.) the workflow.

Step 250 includes the broker 150 calculating or comparing bids generated by the bidding engine 140 so as to allocate or assign each of the patients 105 to each of the slots in the schedule of the resources 110, 112, 114, or vice versa, the allocation of the resources 110, 112, 114 to the schedule of each of the patients 105. The broker 150 may also alter, modify, suggest, or cancel one or more events in the workflow via tracking of one or more properties 116, 118, 120, 121 of the resources 110, 112, 114 or patient 105 in relative to time and the workflow, or change the bids of one more patients 105 or resources 110, 112, 114 dependent on updated changes to tracked data of one or more properties 116, 118, 120, 121.

Figure 3:
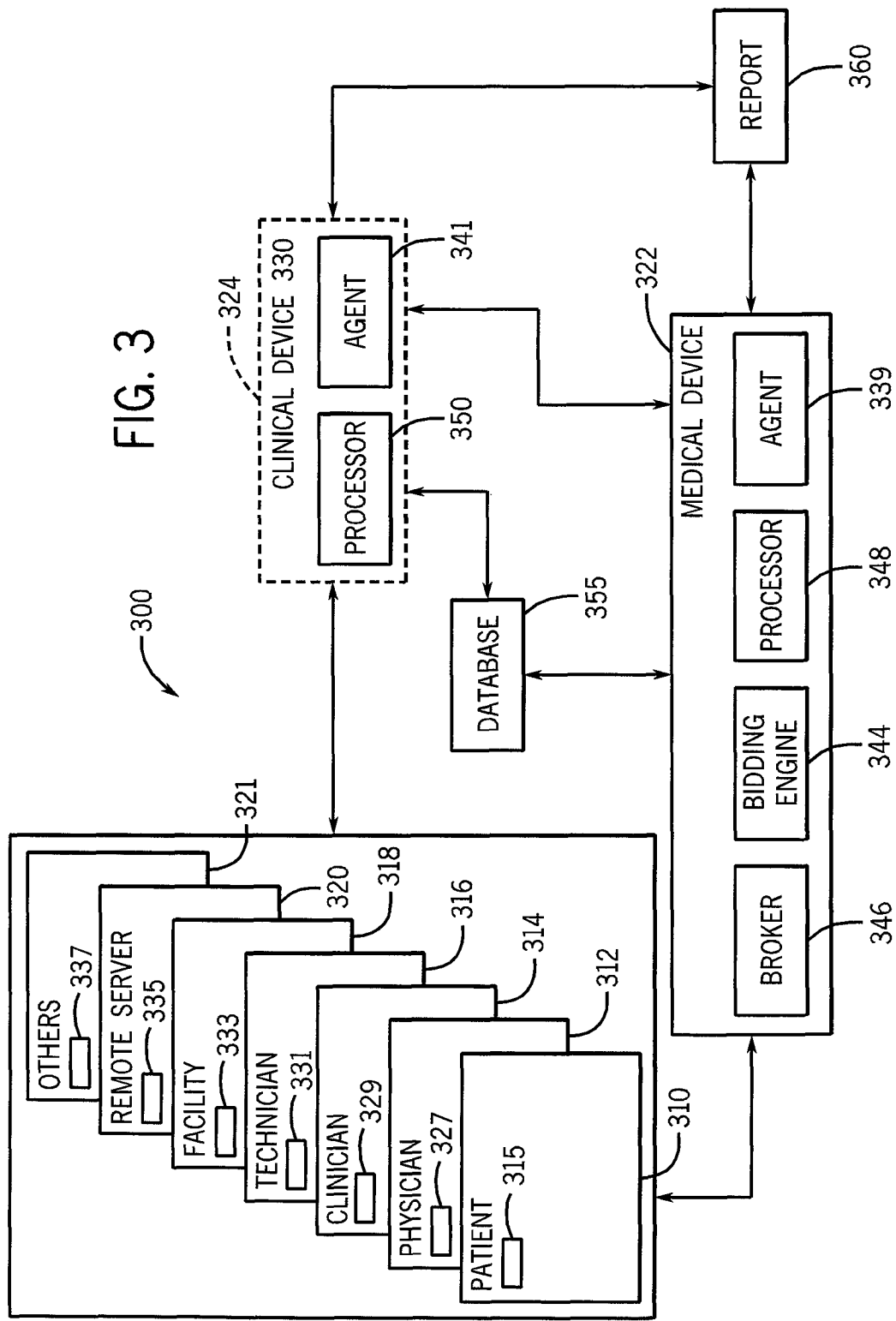
FIG. 3 is a schematic diagram illustrating another embodiment of a system to manage a workflow in a clinical environment.

FIG. 3 illustrates an embodiment of a system 300 to manage a workflow in a clinical environment, similar to the system 100 described above. An example of workflows in a clinical environment includes a nuclear medicine cardiac study comprised of a succession of steps, and potential wait times between each phase of the study.

The workflow requested by a patient 310 can include the following resources: a physician 312, clinician 314, technician 316, facility 318, remote server 320, a medical equipment or device 322, and a clinical equipment or device 324. Of course, the types and number of resources 312, 314, 316, 318, 320, 322, and 324 can vary. Properties identified or assigned to be tracked for each patient 310 at the time of admission or registration can include a patient priority classification as a chronic versus critical condition, an ability to exercise, a predicted stress test time for cardiac evaluation, weight, etc. in accordance to information provided by the patient 310 in a simple self-assessment questionnaire, similar to the properties 116, 118, 120, 121 described above. The properties can also include a liver clearance time or other proxies calculated in the case of a Nuclear Medicine study workflow.

Agents 325, 327, 329, 331, 333, 335, 337, 339, 341 can be created to track the one or more dynamic properties of each respective resources 310, 312, 314, 316, 318, 320, 322, 322, 324. An embodiment of the patient agent 325 tracks different properties of the patients 310 to which it is associated, and calculates a representative current state of activity of the patient 310. The patient agent 325 is in communication with other agents 327, 329, 331, 333, 335, 337, 339, 341 of the system 300. The agents 325, 327, 329, 331, 333, 335, 337, 339, 341 interact or communicate with one another to calculate a priority status of patient 310 to each of the resources 312, 314, 316, 318, 320, 322, 322, 324 relative to other patients 310 admitted to the workflow. The patient agents 325, 327, 329, 331, 333, 335, 337, 339, 341 may themselves calculate each priority status or in combination with the help of the server 335. The agent 325 can track the dynamic properties on an as-need basis, period basis, or continuously through the workflow. For example, if the property of the patient 310 is classified in critical condition, the agent 325 can track the patient's blood pressure every five minutes, and this time interval can adjust with changes in the blood pressure.

The system 300 also includes a bidding engine or scheduler 344 and a broker 346, similar to the bidding engine 140, and broker 150 of the system 100 described above. If the property of the patient 310 is classified or identified or calculated as an emergency or critical, the agent 325 or the bidding engine 344 may automatically calculate or assign a highest priority status to the patient 310 to push through the workflow at a reduced time relative to other patients. In another example, if a property or bidding policy is representative of a maximum wait time of the patient 310 is set for three hours prior to or during the workflow, then even if the patient is otherwise of a low priority status based on the other properties, the bidding engine 344 may increase the bid so as to cause broker 346 to and schedule the patient 310 ahead of others waiting for the medical or clinical device 322 or 300, respectively.

An embodiment of the medical device 322 can include a processor 348 generally operable to execute the functions (represented as computer readable program instructions) of the medical device 322 or agent 339. An embodiment of the clinical device 324 can also include a processor 350 that executes functions (represented as computer readable program instructions) of the clinical device 324 or agent 341. An embodiment of the agent 339 created in correspondence to the medical device 322 can be operable to track at least one property, including a failure status, or a patient handling capacity of the medical device 322. In such a situation, the agents 325, 327, 329, 331, 333, 335, 337, 339, 341 can collaborate or communicate with one another to calculate or create a priority status of the patient 310 to each of the medical device 322 or the clinical device 324 relative to one another.

The patient agent 325 communicates the priority status of each patient 310 to the bidding engine 344. The bidding engine 344 also receives the priority status from the agents 327, 329, 331, 333, 335, 337, 339, 341 correlated to the respective physician 312, clinician 314, technician 316, facility 320, medical device 322 or clinical device 324. Dependent on the received priority statuses, the bidding engine 344 calculates the bid, as described above, of each patient 310 for an opportunity to one of the slots in the schedule of the one or more of the physician 312, clinician 314, technician 316, facility 318, remote server 320, a medical equipment or device 322, and clinical equipment or device 324, or vice versa, similar to the bidding engine 140 of the system 100 described above. The bidding engine 344 can be located at either the medical device 322 or the clinical device 324 or at a server associated therewith.

In accordance with one or more bidding policies created for the workflow and the series of received priority statuses, the bidding engine 344 can identify the multiple schedule combinations that employ the one or more patients 310 in the slots of the schedule of the physician 312, clinician 314, technician 316, facility 320, medical device 322 or clinical device 324. The bid of each patient 310 to slots in the schedule of each of the physician 312, clinician 314, technician 316, facility 320, medical device 322 or clinical device 324 can be altered at any time with a change in a tracked property, and the bidding engine 344 can re-calculate the slots in the schedules accordingly so as to increase but not overload a patient handling capacity of the physician 312, clinician 314, technician 316, facility 320, medical device 322 or clinical device 324, or to reduce the wait time of each patient 310, and to increase the overall capacity of the workflow.

Another example of a property that can be tracked by one of the patient agents 325 includes a need (e.g., patient in critical or emergency condition) to expedite a clinical study (e.g., catheter lab). Having tracked a change in the expedited need property of the patient 310, the agent 325 can collaborate with the other agents 327, 329, 331, 333, 335, 337, 339, 341 to re-calculate the priority status of each, and automatically communicate the changes in the priority statuses to the bidding engine 140. The tracked property or measured value or status (e.g., expedited need or critical condition of the patient 310) can be modified throughout the progression through the sequence of steps in workflow (e.g., clinical study). Tracked data acquired during progression through the sequence of steps can be encoded in a patient record and stored in at the database 355 (e.g., picture archival system, electronic medical record (EMR), etc.). Dependent on changes in the tracked data, the agents 327, 329, 331, 333, 335, 337, 339, 341 track (e.g., continuously, periodically, etc.) communicate collaborative changes in the priority status of each to the bidding engine 344, thereby contributing to the bidding engine 344 calculating bids that can push or increase the priority status of one patient 310 relative others. In this way, the system 100 can track and schedule according to slices of events or time in the workflow of the study relative to changes in the criticality of the health or emergency of each of the patients 310 and changes to the availability of patients 310 or the physician 312, clinician 314, technician 316, facility 320, medical device 322 or clinical device 324.

The broker 346 is generally operable to review or re-calculate or adjust or change the assignment of one or more of the patients 310 to slots in the schedule of each of the medical devices 322 or clinical devices 324 with every completion of an event or step (e.g., a test) in the workflow. The broker 346 can also identify or detect the patient 310 with the highest priority status in accordance to the bid generated by the bidding engine 344 relative to properties tracked by the system 300, including a capacity of the workflow, the wait-time, the time to process through the workflow, etc. For example, each of the bids of each of the patients 310 to each slot in the scheduled period of operation of the resources 310, 322, 324, based on properties, current condition, applicability for the sequence of steps or events in the study or test and their derived current priority. Each patient 310 may be given an output device (e.g., pager, email device, etc.) or number to signal their assignment to the slot in the study or test. Accordingly, the bidding engine 344 in combination with the broker 346 negotiates and re-negotiates how the each patient 310 is assigned to the slots of scheduled operation of the medical device 322 or clinical device 324 of the system 300, or vice versa, with changes in the tracked properties of each patient 310 or resources 310, 322, 324.

Further, additional bidding policies or rules or properties (e.g., with respect to the bids or schedule of the medical device 322 or clinical device 324) to track the relative wait times on each of the remaining patients 310 so as to create or cause boundary conditions such that no patient 310 times-out (i.e., exceeds the maximum wait time) relative to eligibility to the respective resource 310, 322, 324, such as in the case of injection of biophysical markers (i.e. nuclear medicine), or priority relative to a criticality of diagnostic need.

The system 300 is also operable to analyze and create a report 360 (e.g., graphic display on a monitor, printout, etc.) of the tracked properties described above to track a performance/efficiency of or trends in the workflow relative to changes in admissions or patient populations, different patient groupings, changes in availability of resources 310, 322, 324, changes in procedure, etc. Accordingly, the system 300 can calculate and report metrics or trends, based on acquired data of the various properties described above, to predict or increase a throughput of the workflow relative to a patient population and groupings over a period of time. Other metrics that can be tracked and reported by the system 300 include costs versus throughput of admission (e.g., number per day, time per patient) in the workflow.

In view of the report 360 of tracked metrics and trends in the properties described above, the bidding policies can be altered, added, or deleted to re-define or change the rules directed to reducing the wait time of the patient 310 or to increase the availability of resources 310, 322, 324 in the workflow. The broker 346 is generally operable to change bidding policies when the system 300 is stressed beyond a normal or predetermined operating capacity that may be associated with a demographic shift in service area for a nuclear medicine machine that may otherwise cause lower than expected efficiency. The broker 346 is operable to track deviations in the tracked properties or priority statuses or schedule of the physician 312, clinician 314, technician 316, facility 320, medical device 322 or clinical device 324. The broker 346 is also operable to simulate or model the properties, priority statuses, schedule so as to calculate resulting progress of patients 310 through the workflow according to a new or change in bidding policy of the system 300. The broker 346 can calculate the above-described simulations periodically in time, or with arrival of each patient or admission in the workflow, and track changes in the simulated values relative to realized values.

An embodiment of the system 300 can be operable to manage a workflow that comprises several workflows among several medical facilities. For example, the workflow can include a workflow through a trauma unit, a workflow through an emergency unit or room, and a workflow through an urgent care unit where there is overlap in services or steps/events of the workflow. According to the tracked properties of each of the patients 310, the physician 312, clinician 314, technician 316, facility 320, medical device 322 or clinical device 324, the system 100 is operable to evaluate various combinations of scheduling the one more patients to one or more of the patient 310, the physician 312, clinician 314, technician 316, facility 320, medical device 322 or clinical device 324 employed among the various workflows (e.g., trauma, emergency, urgent care) described above that is most efficient (e.g., lowest patient wait time, largest throughput of admissions, etc.) in view of predicted trends calculated from historical data of the tracked properties of the physician 312, clinician 314, technician 316, facility 320, medical device 322 or clinical device 324 and of the patients 310 (e.g., peak demand at particular times, etc.).

Figure 4:
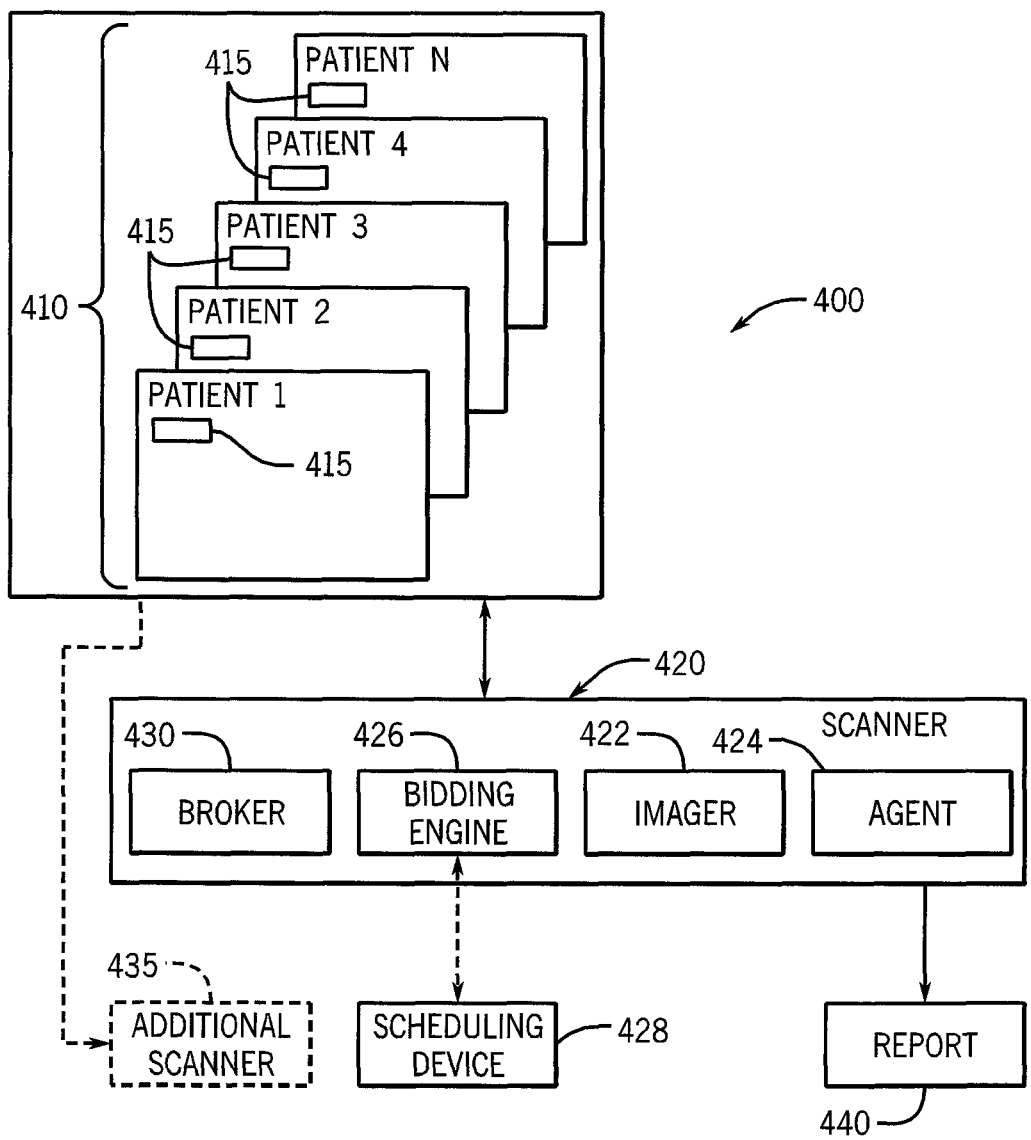
FIG. 4 is a block diagram illustrating another embodiment of a system to manage a workflow to schedule a patient to undergo medical imaging.

FIG. 4 illustrates another embodiment of a system 400 to manage scheduling of a series of patients 410 through a workflow. An agent 415 is created for each patient 410 so as to track at least several of the properties identified for the patients 410, similar to the agents 127 and 325 described above. The agent 415 can be created at the beginning of the workflow in accordance to the clinical procedure (e.g., list of properties are predetermined, identified, and stored for each of a series clinical procedures for later recall per an input at the admission of the patient 410). Various types of properties (e.g., ability to exercise) can be measured, added or deleted from tracking by the patient agent 415 in accordance to data acquired from self-screening or in conducting a preliminary screening of the patient 410. Examples of static properties include the patient's age, a maximum wait time, a usage of a pacemaker, etc. Examples of dynamic properties that may change with time include an injury to the patient, blood pressure, criticality of the patient 310, change in consciousness, time limits associated with use of nuclear medicines or markers, etc. One or more patient properties may be created in general real time during progression through the steps or events of the workflow. For example, if the patient 410 starts to bleed, the agent 415 may create a property to track a degree of bleeding of the patient 410, which otherwise may not have been defined as a property at the time of admission or prior to start of the workflow (e.g., diagnostic imaging, clinical study, catheterization, etc.).

Assume for sake of example, the workflow of the patients 410 employs a scanner 420 used in medical imaging. An embodiment of the scanner 420 includes an imager 422 (e.g., CT imaging system, PET imaging system, x-ray imaging system, MR imaging system, ultrasound imaging system, etc.) that generally performs the imaging function of the scanner 420. A scanner agent 424 is created to track one or more properties of the scanner 420 or imager 422 employed in the clinical procedure. For example, the scanner agent 424 can track a capacity of the scanner 420, or a failure status of the scanner 420. The scanner agent 424 is operable to communicate or collaborate with each of the patient agents 415 directed to each of a series of patients 410, as well as other agents (not shown) directed to other medical or clinical devices (not shown).

The embodiment of the system 400 also includes a bidding engine 426, similar to the bidding engines 140 and 344 described above. In accordance to the priority statuses communicated by the agents 415 of the patients 410 and the agent 424 of the scanner 420 (e.g., capacity), the bidding engine 426 creates or calculates a bid value of each patient 410 for a slot in the schedule of the scanner 420. In creating the schedule of slots, the bidding engine 426 complies with predetermined or added bidding policies that generally define boundary conditions of the patient 410, scanner 420, and workflow. Alternatively, another embodiment of the bidding engine 426 can communicate with a scheduling device 428 to assign or identify each patient 410 to respective slots in the schedule of use or availability of the scanner 420. The bidding engine 426 is operable to re-create or change the schedule in accordance to unpredicted changes in the priority statuses that may occur as the patients 410 progress through the workflow (e.g., clinical procedure). For example, if the patient agent 415 communicates to change one of the patients 410 to a critical condition and associated high priority status, the bidding engine 426 at any point in time of the workflow can recalculate the bids for the one or more of the series of patients 410 such that the high priority patient 410 progresses at the highest priority status through events (e.g., schedule of the imager 422) of the workflow in the least amount of wait time relative to the other lower priority status patients 410.

The system 400 can also include a broker 430 in communication with the bidding engine 426 and agents 415, 424 of the patient 410 and scanner 420, respectively. If a capacity of the scanner 420 is limited, the broker 430 may generate a message or report or purchase order that requests addition of another scanner 435 (shown in dashed line) to the workflow. The broker 430 can also be operable to modify the steps or events of the workflow. For example, the broker 430 may communicate an instruction that causes the scanner 420 to skip one or two steps in the workflow in response to one or more tracked properties communicated from the agents 415 or 424.

The system 400 is also operable to generate a report 440 of the schedule to each patient 410 or to the technicians or clinicians involved in the workflow. This information can be generated and reported in advance so as to reduce the preparation time of the patients 410 for the clinical procedure. By the time a first patient 410 completes one or more steps of the clinical procedure, a next patient 410 can be prepped and ready according to the schedule. Updates to the schedule can be reported to the patients 415 who have not yet arrived for the clinical procedure or as the changes are made by the bidding engine 426 or broker 430 in response to changes in the tracked properties of the patients 410 or scanner 420 during progression of patients 410 through the workflow.

In another example, assume the workflow includes steps in a process of administering nuclear medicine into the patient 410 to enhance imagine. If the patient agent 415 or scanner agent 424 tracks or detects a change in a patient 410 wait profile such that a number of patients 410 that have received the nuclear medicine exceed a number of untreated patients 410, then the agents 415 and 424 in communication with the bidding engine 426 are operable to modify the schedule of each patients 410 so as to cause the number of treated patients 410 to be reduced relative to the number of untreated patients. The system 400 can also run mixed clinical populations, and use the diagnostic-test request code as part of the mechanism of the bidding engine 426.

Figure 5:
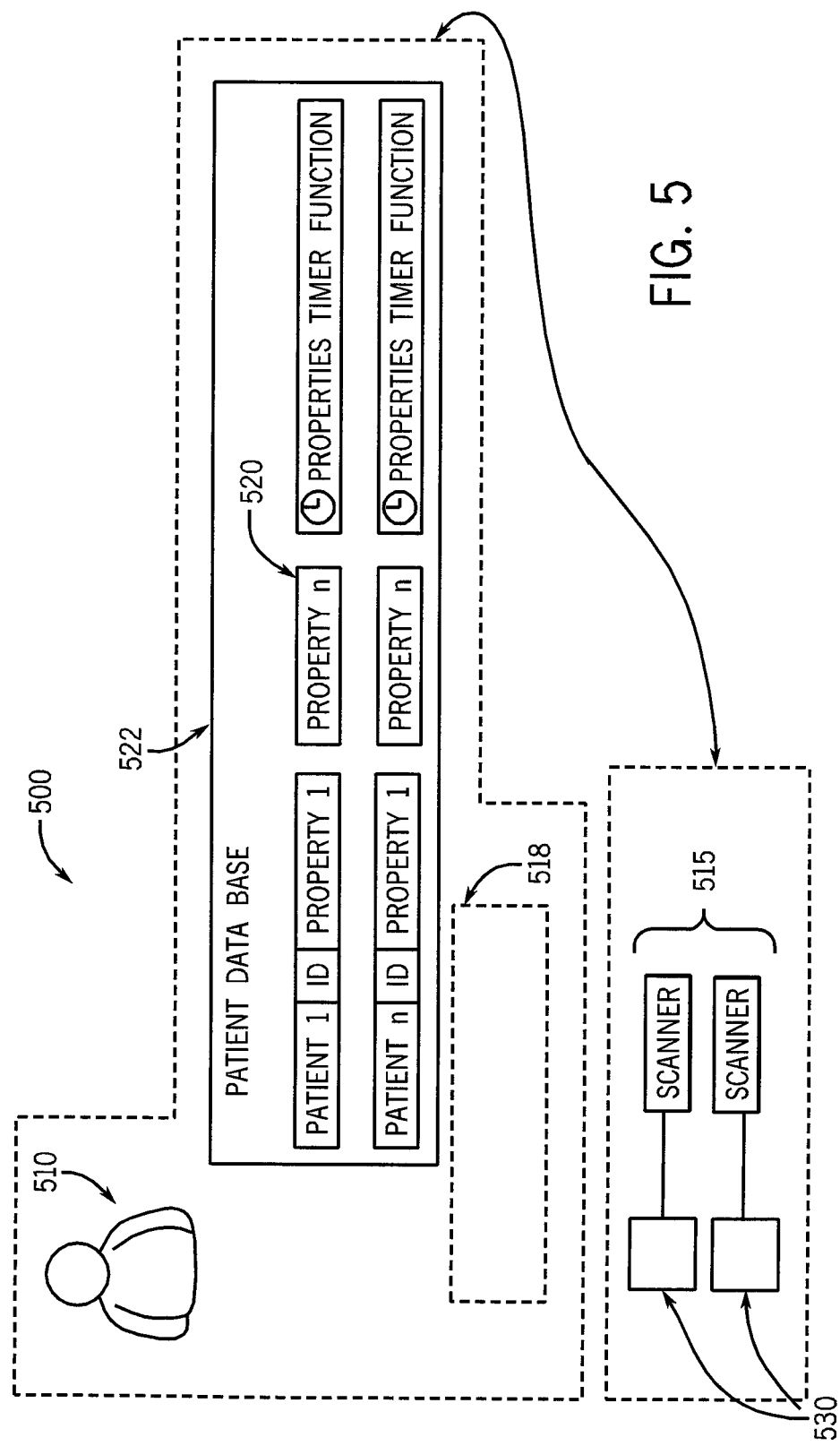
FIG. 5 is a pictorial illustration of another embodiment of a system to manage a workflow in a clinical environment.

FIG. 5 is an illustration of another embodiment of a system 500 to manage a workflow of a patient 510 through a procedure that employs one or more scanners 515. Assume that the system 500 collects or acquires patient information (e.g., patient identification, blood pressure, self/pre-assessment, etc.) from each patient 510 at the time of admission of the patient 510 to the entity (e.g. hospital, clinic). Based on the gathered information, an agent 518 is created to track a series of properties 520 identified for each patient 510. For example, the properties 520 can be identified according to a clinical condition of the patient 510 and/or based on a self/pre-assessment test of the patient 510. The system 500 includes a patient database 522 to store the data of the tracked properties 520 (e.g., patient information such as patient identification (ID), other gathered or tracked information, or measured statuses or values of the various tracked properties by the agent 518). An embodiment of the patient agents 518 can also track the property for a time of waiting and/or progression through the workflow. The properties 520 can also represent a maximum wait period for each patient, where the elapse of the maximum wait period automatically creates a highest priority status to the respective patient 510. Assume that the system 500 includes a scanner agent 530 to track one or more properties (e.g., current capacity) of the one or more scanners 515.

The agents 518 and 530 are operable to sense the presence and awareness, as described above with respect to system 100, so as to communicate and collaborate in general real-time with one another, and to track the properties of the patients 510 and scanner 515 through the workflow. One embodiment of the patient agent 518 communicates a current state of activity of the patient 510 to other agents 518 of other patients 510 or to the agent 530 of the scanner 515. From the collaboration, each patient agent 518 identifies a priority status of each respective patient 510 relative to the others in each of the slots in the scheduled operation of the scanner 515, or simply next in the scheduled operation of the scanner 515.

The scanner agent 530 can be operable to track a failure status or the patient handling capacity or other limiting property (e.g., unavailability of operating technician or physician or clinician) of the scanner 515. The scanner agent 530 is generally configured to establish a general real time interaction between the agents 518 of the patients 510 and the scanner 515. An embodiment of the scanner agent 530 is operable to calculate track the properties of the scanner 515 and the capacity of the scanner 515 (e.g., the capacity of the scanner 515) at a given point of time, and collaborate with agents 530 of other scanners 515 or the agents 518 of the patients 510, and can identify a priority status of the scanner 515 to each patient 510.

Figure 6:
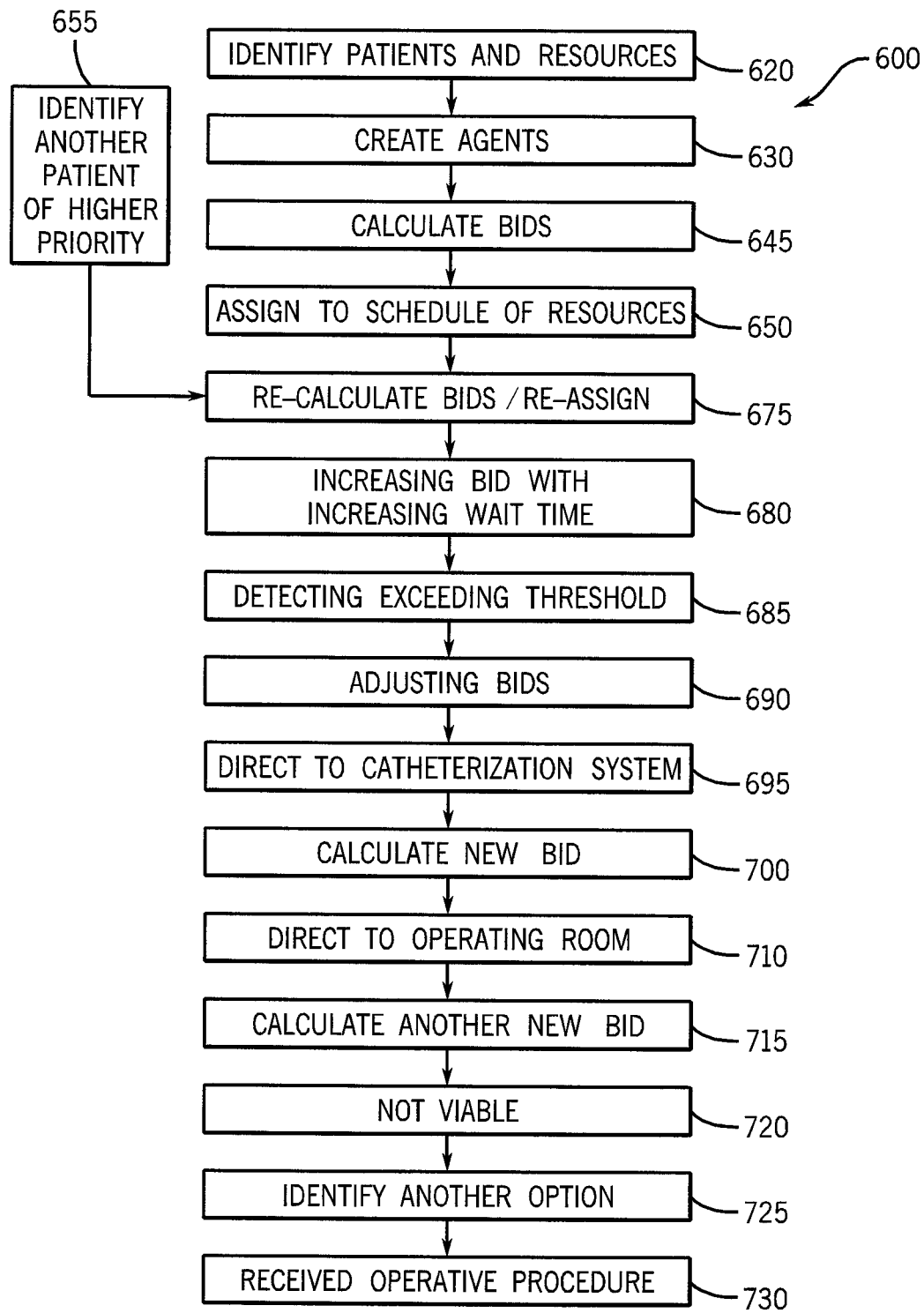
FIG. 6 is a flowchart illustrating another embodiment of a method of managing a workflow to schedule patients for a clinical procedure.

FIG. 6 includes a schematic flow diagram illustrative of another embodiment of a method 600 to manage progression of the patient 610 with chest pain through the workflow of events employing resources 110, 112, 114 as shown in FIG. 1. Assume for sake of example that the illustrated embodiment of resources are as follows: a physician 110, an operating room 112, and a cardiac catheterization system 114.

Step 620 includes identifying the patient 105 admitted and the availability of the resources 110, 112, 114. Of course, the number of patients 105 and resources 112, 114, 116 can vary. Step 620 can also include identifying the set of properties 121 (e.g., a patient handling capacity, a wait time, or other factor identifying an unpredicted situation in the workflow, etc.) of each patient 105 or properties 116, 118, 120 of the resources 110, 112, 114 in the workflow.

Step 630 includes creating the agents 127 operable to track the properties 121 of the patients 610, and agents 122, 124, 126 to track properties 116, 118, 120 of the resources 110, 112, 114, respectively, at any point in time of the workflow. The agents 122, 124, 126, 127 communicate or collaborate with each other and communicate a priority status of each patient 105 or resources 110, 112, 114 to the bidding engine 140 at any given time in the workflow.

Step 645 includes the bidding engine 140 calculating the bid of each of the patient 105 for assignment to each slot in the schedule of operation of each resource 110, 112, 114 of the workflow, dependent on the priority statuses communicated from the agents 122, 124, 126, 127. As described above, the bidding engine 140 can be configured to calculate or generate bids of each resource 110, 112, 114 to a slot in the schedule workflow of each of the respective patients 105.

Assume for sake of example, that the patient 105 is admitted with chest pain, and the patient agent 127 is created to track a wait time or one or more symptoms of a heart attack, and step 620 includes identifying the physician 110 as the next critical resource in the workflow to treat the patient 105. Dependent on the priority statuses received by the bidding engine 140, the bidding engine 140 calculates the bid of the patient 105 to each slot of the schedule of the physician 110. Alternatively, the bidding engine 140 may calculate the bid of each patient 105 to be next in the schedule of the physician 110. Step 650 includes the broker 150 calculating or assigning the patient 105 to one of the slots in the schedule of the physician 110 dependent on the bids generated by the bidding engine 140. Or in addition, the broker can compare bids of each of the resources 110, 112, 114 so as to calculate or generate or assign each resource 110, 112, 114 to a slot in the schedule workflow of each of the patients 105.

Step 655 includes another patient (shown in dashed line and by reference 665 in FIG. 6) is admitted to the workflow, and an agent 670 created for the patient 665 tracks that the second patient 665 is in a state of shock. Alternatively or in addition, the agent 670 can be created for each resource 110, 112, 114 introduced into the workflow. According to the greater severity of the tracked state of shock of the patient 665, the patient agent 670 in combination with the patient agent 127 communicates to the bidding engine 140 that the second patient 665 has a higher priority status relative to the first patient 105. In response, step 675 includes the bidding engine 140 re-calculating or updating or altering the bid values of the first patient 105 relative to the second patient 665 such that the broker 150 schedules the second patient 665 to be seen by the physician 110 before the first patient 650. The type of tracked property (e.g., loss of consciousness, etc.) that would trigger the second agent 665 to increase the priority status of the second patient 665 relative the priority status of the first patient 105 can vary.

As the agent 127 tracks an increase in the wait time of the first patient 105 to receive an examination by the physician 110, step 680 includes the bidding engine 140 increasing the bid of the first patient 105 relative to others that have less waiting time to receive an examination by the physician 110. Step 685 includes the agent 127 detecting and communicating that the wait time of the first patient 105 to see the physician 110 has exceeded a threshold. In response, step 690 includes the bidding engine 140 adjusting the bid of the first patient 105 to exceed the bids of others waiting see the physician 110. According to the change in the bid of the first patient 105, the broker 150 assigns the first patient 105 to be assigned the next available slot in the schedule of the physician 110 relative to other patients waiting to see the physician 110.

Step 695 includes receiving an examination and identifying or directing the patient 105 to another resource 112 or 114. Assume that the physician 110 identifies that a degree of arterial blockage of the patient 105 should be measured with the cardiac catheterization system 114. Step 700 includes the agent 127 in combination with the bidding engine 140 calculating a new bid of the first patient 650 for a slot in the schedule of the cardiac catheterization system 114 relative to bids of other patients waiting for the cardiac catheterization system 114. Assume that upon increasing the bid of the first patient 105 with increased waiting time relative to the other patients, the broker 150 schedules the patient 105 in the next available slot in the schedule of the cardiac catheterization system 114.

Assume that examination by the cardiac catheterization system 114 generates an output or report that quantifies an arterial blockage of the first patient 105 that requires an operative procedure. Step 710 includes directing or identifying that the patient 105 is to be directed to the operating room 112 so as to receive the operative procedure to remediate the blockage. Now assume that the system 100 identifies the new properties to tracked by the agent 127 relative to scheduling an opportunity in the schedule of the operating room 112 includes a wait time and the quantified blockage. Dependent on the tracked properties of the patient 105 relative to other patients, step 715 includes communicating a priority status of the patient 105 to the bidding engine 140, comparing the priority statuses received from the agent 127 relative to others, and creating the bid of the first patient 105 for a slot in the schedule of the available operating room 112 relative to other patients scheduled or waiting for the operating room 112.

Step 720 includes the agent 124 of the operating room 112 detecting and communicating to the agent 127, or to the bidding engine 140, or to the broker 150 that a time to wait for the operating room 112 exceeds a threshold (e.g., exceeding capacity, surgeon not available, exceeding threshold wait time, etc.). Step 725 includes the broker 150 identifying or calculating a next available option (e.g., wait in a cardiac care unit (not shown)) until step 730 of receiving the procedure in the operating room 112 and/or completing the scheduled workflow.

FIG. 7 illustrates an embodiment of a dashboard 800 to illustrate output data of the system 100 shown in FIG. 1 and described above. Although described with reference to the system 100, the dashboard can also be part of the systems 300, 400, and 500 described above. The dashboard 800 generally includes an illustration of each patient 105 admitted to the workflow according to an order of value of bids 805 directed to each of a series of slots 810 in the schedule of each of the available resources 110, 112, 114 employed in executing the events of the workflow. An illustration of the values of the bids 805 can also be listed, or the patients 105 can merely be listed in numerical order of value of the respective bids. The dashboard 800 can further include a graphic display generally illustrative of a geographic map 815 of the location, availability and current utilization of each of the resources 110, 112, 114 that can be relative to a location of each patient 105. The embodiment of the dashboard 800 can also include an alarm (e.g., illumination of patient identification in a predetermined color, audible alarm, etc.) indicative that respective agents 127 report that one or more of the patients 105 exceeds a predetermined threshold (e.g., wait time) or is tracked to be in or approaching a predetermined critical condition (e.g., unconscious, threshold loss or increase in blood pressure, cardiac arrhythmia, etc.). Any of the above-described tracked or calculated parameters can be illustrated in various combinations with one another at the dashboard 800.

FIG. 8 illustrates another embodiment of a dashboard 900 for graphic display on a monitor or screen or other known similar device to an operator. The dashboard 900 is generally configured to illustrate output data of the system 100 shown in FIG. 1 and described above. Although described with reference to the system 100, the dashboard can also be part of the systems 300, 400, and 500 described above. The dashboard 900 generally includes an illustration of each of the value of bids 905 generated by the bidding engine 140 for each of the one or more of the resources 110, 112, or 114 directed to each of a series of slots 910 in the schedule workflow of each of the patients 105. As described above, the bidding engine 140 generates the bids dependent on received data of the tracked properties of the resources 110, 112, 114 (e.g., location of resource relative to patient, failure condition, under repair or scheduled for maintenance after detected number of uses, dirty vs. clean, in current use, etc.) or patient 105. An illustration of the values of the bids 905 can be listed merely in numerical order of value. The dashboard 900 can further include a graphic display generally illustrative of a geographic map 915 of the location, availability and current utilization of each of the resources 110, 112, 114 that can be relative to a location of each patient 105. The embodiment of the dashboard 900 can also include an alarm (e.g., illumination of patient identification in a predetermined color, audible alarm, etc.) indicative that respective agents 127 report that one or more of the patients 105 exceeds a predetermined threshold (e.g., wait time) or is tracked to be in or approaching a predetermined critical condition (e.g., unconscious, threshold loss or increase in blood pressure, cardiac arrhythmia, etc.). Any of the above-described tracked or calculated parameters can be illustrated in various combinations with one another at the dashboard 900.

A technical effect of the above-described systems 100, 300, 400, and 500 and methods 200 and 600 is to manage a workflow and respond to various changes in the properties of the resources (including patients) or workflow in general real-time. Although the systems 100, 300, 400 and 500 and methods 200 and 600 are described with respect to specific healthcare environment, systems 100, 300, 400 and 500 and methods 200 and 600 can be extended to any nature or type of workflow. Other examples include diagnostic equipment that supports multiple test types reconfigures self to support high priority patient need. Alternatively, a department schedule can have one operational profile one day or even one hour to suit a demand, and be reprogrammed with another operational schedule to suit a different demand in time. The systems and methods are also operable to create a schedule that accommodates combination or permutations of conditions. Thereby, the systems and methods afford huge flexibility and control of a workflow relative to those managed as only a linear function.

Another technical effect of the above-described systems 100, 300, 400, and 500 and methods 200 and 600 to manage a workflow includes generating a dynamic schedules based on dynamic properties of the resources involved in the process. In clinical workflows the dynamic properties can include a patient's current clinical condition and/or the static conditions identified at admission through self/pre-assessments. The above-described systems 100, 300, 400, and 500 and methods 200 and 600 are also operable cope with variance in patient wait time and processing time relative to progression of tests and dynamic patient properties.

Another technical effect of the above-described systems 100, 300, 400, and 500 and methods 200 and 600 to manage a workflow is to facilitate enhanced management of workflows, generally in real time, where the workflow might otherwise tend toward chaos due to complex conditions that evolve in general real time beyond the original workflow design.

Another technical effect of the above-described systems 100, 300, 400, and 500 and methods 200 and 600 to manage a workflow includes employing a dynamic bidding process in general in general real-time to manage the workflow. The above-described systems 100, 300, 400, and 500 and methods 200 and 600 include defining dynamic properties, tracking their properties in real time, assigning a relative priority status considering the properties of other resources or patients and bidding for opportunities dependent on those priority statuses. The bidding policies can change dependent on, among other things, tracked properties of the various resources.

Yet another technical effect of the above-described systems 100, 300, 400, and 500 and methods 200 and 600 an ability to manage the execution of the workflow in an adaptive manner. The above-described systems 100, 300, 400, and 500 and methods 200 and 600 are operable to change various events/steps of the workflow in general real time based on the tracked properties of the resources and patients in the workflow. For example, the above-described systems 100, 300, 400, and 500 and methods 200 and 600 are driven by dynamic changes in capacity of the resources and conditions of the patients.

Another technical effect of the above-described systems 100, 300, 400, and 500 and methods 200 and 600 includes an ability to change the operational profile of the various resources such as medical equipment involved in the workflow dependent on the properties of the patient or equipment. For example, the system 100, 300, 400, and 500 are operable to reconfigure diagnostic equipment that otherwise support multiple test types to instead support a high priority patient need, or to schedule patients on a basis of expected test times or steps along in the test sequence.

Yet another technical effect of the above-described systems 100, 300, 400, and 500 and methods 200 and 600 is to measure and increase a throughput of patients through a department or unit dependent on changes in the equipment, procedure, patient population and so on. Yet another technical effect of the above-described systems 100, 300, 400, and 500 and methods 200 and 600 is extending capacity by adding similar systems in real time dependent on the tracked capacity of and load to be handled by the resources 110, 112, 114 at the given point in time.

Yet another technical effect of the above-described systems 100, 300, 400, and 500 and methods 200 and 600 include an ability to test permutations or simulations in response to the dynamic properties of the patient population relative to need for service.

Yet another technical effect of the above-described systems 100, 300, 400, and 500 and methods 200 and 600 includes providing an ability to employ a real time bidding techniques to manage a workflow, including defining dynamic properties to each bidder, tracking their properties in real time, assigning a relative priority status considering the properties of other resources, and bidding for an opportunity based priority status. To resolve the priority status or to assign the opportunity, a set of bidding policies are implemented dependent on static and dynamic properties of the patients and resources in the workflow at a given time.

Although the subject matter is described herein with reference to medical diagnostic or cardiac treatment applications, it should be noted that the subject matter is not limited to this or any particular application or environment. Rather, the subject matter may be employed or applied to any service provider to manage scheduling of multi-variant or non-linear workflows. Examples include workflows employing an ultrasound diagnostic system, on-line trading wherein buyers and sellers keep on adding and removing from the process, supermarkets, ambulatory or other emergency service, etc. Also, it should be understood that one or more of the steps or components of one of the systems 100, 300, 400, and 500 and methods 200 and 600 and dashboards 800 and 900 described above can be used with another of the method or systems or dashboards described above and is not limiting on the invention.

This written description uses examples to disclose the subject matter, including the best mode, and also to enable one skilled in the art to make and use the invention. The patentable scope of the subject matter is defined by the following claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

We claim:

1. A system to manage progression of a plurality of patients through a workflow of events that employs a plurality of resources to deliver healthcare to the plurality of patients, comprising:
   a plurality of agents associated with the plurality of resources, at least one agent to track at least one property of at least one of the plurality of resources, the plurality of agents communicatively coupled to each other to communicate the at least one tracked property of the respective resource among the plurality of agents and to assign priority statuses to each of the resources, wherein the priority statuses indicate a priority of each of the resources relative to the other resources with respect to a slot in a schedule of the workflow of at least one patient, wherein one of the plurality of resources comprises a medical diagnostic system, and wherein the at least one property includes at least one of (1) a measured wait time of the at least one patient, (2) a critical condition of the at least one patient, (3) a degree of progression of the at least one patient through the workflow events, (4) a patient handling capacity of each of the plurality of resources, (5) a status of use of each of the plurality of resources or (6) a failure condition of each of the plurality of resources; and
   a processor in communication with the plurality of agents, the processor to execute computer readable program instructions in a non-transitory memory to:
      calculate bids for the plurality of resources directed to the slot in the schedule of the workflow of the at least one patient, the bids dependent on (1) the at least one tracked property of the at least one of the plurality of resources and (2) the priority statuses of the respective resources of the plurality of resources with respect to the other resources, wherein calculating the bids includes continually monitoring at least one property of at least one the plurality of resources in real time during the workflow and dynamically updating the bids in real time during the workflow based on changes to the at least one tracked property; and
      assign one of the plurality of resources to the slot in the schedule of the workflow of the at least one patient based on a comparison of the dynamically updated, real-time bids of the plurality of resources to one another.

2. The system of claim 1, wherein the bids are based on at least one property of at least one of the plurality of patients, the at least one patient property comprising at least one of a time of progression through the workflow, a wait time to begin the workflow, a classification of the patient need as critical versus non-critical or a time of treatment with a contrast agent or a nuclear medicine.

3. The system of claim 1, wherein each of the bids represents a value indicative of an availability to be employed in the workflow relative to another resource.

4. The system of claim 1, wherein the plurality of resources includes a first medical imaging system and a second medical imaging system, and wherein the bids include one bid representative of a value of a priority of the first medical imaging system relative to the second medical imaging system to be assigned to a slot in a schedule of the at least one patient in the workflow.

5. The system of claim 4, wherein calculating the one bid is based on at least one of a patient handling capacity, a status of utilization, a failure condition of the first medical imaging system or a failure condition of the second medical imaging system.

6. The system of claim 1, wherein one of the bids is representative of a priority status of a first resource to be assigned to a slot in a schedule of at least one workflow event of the at least one patient relative to the priority of a second resource to be assigned to the slot in the schedule of the at least one workflow event of the at least one patient, wherein the bid is based on at least one of a measured wait time of the at least one patient, a critical condition of the at least one patient or a location of each of the first resource and the second resource relative to the at least one patient.

7. The system of claim 6, wherein the processor is to create the plurality of agents to track each of the at least one property of the respective resources.

8. The system of claim 1, wherein each of the plurality of agents is to track the at least one property of each of the plurality of resources through the progression of workflow events.

9. A method to manage progression of at least one patient through a workflow of events that employs a plurality of resources to deliver healthcare to the patient, comprising:
tracking at least one property of at least one of the plurality of resources, wherein a plurality of agents is associated with the plurality of resources and at least one of the plurality of agents is to track the at least one property of a respective resource, wherein one of the plurality of resources comprises a medical diagnostic system, and wherein the at least one property includes at least one of (1) a measured wait time of the at least one patient, (2) a critical condition of the at least one patient, (3) a degree of progression of the at least one patient through the workflow events, (4) a patient handling capacity of each of the plurality of resources, (5) a status of use of each of the plurality of resources or (6) a failure condition of each of the plurality of resources;
calculating a priority status for each of the respective resources relative to the other resources, wherein the plurality of agents communicate the at least one tracked property among the plurality of agents to calculate the priority statuses via a collaboration of the plurality of agents, wherein the priority statuses indicate a priority of each of the resources relative to the other resources with respect to a slot in a schedule of the workflow of the at least one patient;
calculating, using a processor, bids for the plurality of resources directed to the slot in the schedule of the workflow of the at least one patient, the bids dependent on the at least one tracked property of the at least one of the plurality of resources and the priority statuses of the plurality of resources with respect to the other resources of the plurality of resources, wherein calculating the bids includes continually monitoring the at least one tracked property of the at least one of the plurality of resources in real time during the workflow and dynamically updating the bids in real time during the workflow based on changes to the at least one tracked property; and
assigning one of the plurality of resources to the slot in the schedule of the workflow of the least one patient based on a comparison of the dynamically updated, real-time bids of the plurality of resources to one another.

10. The method of claim 9 further comprising tracking at least one property of the at least one patient, wherein the at least one property of the at least one patient comprises at least one of a time of progression through the workflow, a wait time to begin the workflow, a classification of the at least one patient's need as a critical versus non-critical condition or a time of treatment of the at least one patient with a contrast agent or a nuclear medicine in anticipation of image acquisition, and wherein calculating the bids is based on the at least one property of the at least one patient.

11. The method of claim 9, wherein each of the bids of the plurality of resources represents a value indicative of an availability to be utilized in the workflow of the at least one patient relative to another of the plurality of resources, and wherein the availability depends on at least one of a handling capacity, a failure condition or a location of the plurality of resources.

12. The method of claim 9, wherein the plurality of resources comprises a first medical imaging system and a second medical imaging system, and wherein the bids include one bid representative of a value of priority of the first medical imaging system relative to the second medical imaging system to be assigned to a slot in a schedule of the workflow of events.

13. The method of claim 12, wherein the one bid is based on at least one of a patient handling capacity, a status of use or operation, a failure condition of the first medical imaging system or a failure condition of the second medical imaging system.

14. The method of claim 9, wherein each of the bids is representative of a priority status of respective resource to the at least one patient dependent on a location and at least one of an availability of utilization of the plurality of resources relative to the at least one patient, a patient handling capacity of the plurality of resources, a detection of a failure condition of the plurality of resources, a measured wait time of the at least one patient for each of the plurality of resources utilized in one of the workflow events, a critical condition of the at least one patient or a degree of progression of the at least one patient through the workflow.

15. The method of claim 14 further comprising collaborating amongst the agents with one another to identify the priority statuses of the plurality of resources relative to one another at any particular time of the workflow events.

16. The method of claim 9 further comprising:
introducing a new resource into the system;
communicating a tracked property of the new resource among the agents of the plurality of resources; and
recalculating the priority statuses of the plurality of resources based at least in part on the tracked property of the new resource.

17. The method of claim 9 further comprising detecting a change in a tracked property in the at least one of the plurality of resources and recalculating the priority statuses of the plurality of resources based at least in part on the changed tracked property of the at least one of the plurality of resources.

18. A dashboard to manage progress of at least one patient through a workflow of events in delivering healthcare, comprising:

a patient identifier illustration of at least one patient;
resource identifier illustrations of a plurality of resources designated to be utilized on the at least one patient progressing through the events of the workflow, the resource identifier illustrations arranged according to an order of value of dynamically updated, real-time bids of the plurality of resources, calculated by a processor and directed to utilization on the at least one patient in the workflow, the dynamically updated, real-time bids of the plurality of resources dependent on (1) at least one continually monitored, tracked property of at least one of the plurality of resources and (2) priority statuses of the respective resources of the plurality of resources with respect to the other resources, and wherein the arrangement of the resource identifier illustrations are dynamically updated during progression of the patient through the events of the workflow based on a change in the priority statuses resulting from a change in the at least one continually monitored, tracked property during the workflow, the priority statuses assigned via a collaboration of a plurality of agents operable to track at least one property of at least one of the plurality of resources, wherein the plurality of agents are operable to communicate the at least one track property to each other, wherein the priority statuses indicate a priority of each of the resources relative to the other resources with respect to a slot in a schedule of the workflow of the at least one patient, wherein one of the plurality of resources comprises a medical diagnostic system, and wherein the at least one property includes at least one of (1) a measured wait time of the at least one patient, (2) a critical condition of the at least one patient, (3) a degree of progression of the at least one patient through the workflow events, (4) a patient handling capacity of each of the plurality of resources, (5) a status of use of each of the plurality of resources or (6) a failure condition of each of the plurality of resources; and a processor to provide instructions to display the patient identifier illustration and the resource identifier illustrations.

19. The dashboard of claim 18 further comprising an alarm to indicate that the at least one patient exceeds a predetermined threshold of wait time.

* * * * *